(12) United States Patent
Baril et al.

(10) Patent No.: US 11,406,369 B2
(45) Date of Patent: Aug. 9, 2022

(54) TISSUE SPECIMEN RETRIEVAL DEVICE WITH REINFORCED SPRING

(71) Applicant: Covidien LP, Mansfield, MA (US)

(72) Inventors: Jacob C. Baril, Norwalk, CT (US); Saumya Banerjee, Hamden, CT (US); Matthew A. Dinino, Newington, CT (US); Justin J. Thomas, New Haven, CT (US); Roy J. Pilletere, North Haven, CT (US)

(73) Assignee: COVIDIEN LP, Mansfield, MA (US)

( * ) Notice: Subject to any disclaimer, the term of this patent is extended or adjusted under 35 U.S.C. 154(b) by 199 days.

(21) Appl. No.: 16/843,782

(22) Filed: Apr. 8, 2020

(65) Prior Publication Data

US 2021/0315560 A1 Oct. 14, 2021

(51) Int. Cl.
*A61B 17/00* (2006.01)

(52) U.S. Cl.
CPC .......... *A61B 17/00234* (2013.01); *A61B 2017/00287* (2013.01); *A61B 2017/00867* (2013.01); *A61B 2017/00991* (2013.01)

(58) Field of Classification Search
CPC .... A61B 17/00234; A61B 2017/00287; A61B 2017/00862; A61B 2017/00867; A61B 2017/00991
See application file for complete search history.

(56) References Cited

U.S. PATENT DOCUMENTS

| 5,354,303 | A | * | 10/1994 | Spaeth ............. A61B 17/00234 |
|           |   |   |         | 604/171 |
| 6,059,793 | A |   | 5/2000  | Pagedas |
| 6,156,055 | A |   | 12/2000 | Ravenscroft |
| 6,162,209 | A |   | 12/2000 | Gobron et al. |
| 6,171,317 | B1 |  | 1/2001  | Jackson et al. |
| 6,206,889 | B1 |  | 3/2001  | Bennardo |
| 6,224,612 | B1 |  | 5/2001  | Bates et al. |
| 6,228,095 | B1 |  | 5/2001  | Dennis |
| 6,248,113 | B1 |  | 6/2001  | Fina |
| 6,258,102 | B1 |  | 7/2001  | Pagedas |
| 6,264,663 | B1 |  | 7/2001  | Cano |
| 6,270,505 | B1 |  | 8/2001  | Yoshida et al. |
| 6,280,451 | B1 |  | 8/2001  | Bates et al. |
| 6,344,026 | B1 |  | 2/2002  | Burbank et al. |

(Continued)

*Primary Examiner* — Mohamed G Gabr
(74) *Attorney, Agent, or Firm* — Carter, DeLuca & Farrell LLP

(57) ABSTRACT

A tissue specimen retrieval device includes first and second shafts telescopically movable relative to one another. The second shaft supports an end effector that is movable relative to the first shaft between a retracted position, wherein the end effector is disposed within the first shaft, and a deployed position, wherein the end effector extends distally from the first shaft in an expanded configuration. The end effector includes a bag brim having first and second ends that operably engage the distal end of the second shaft. The bag brim is transitionable from a first collapsed configuration for disposition within the first shaft to an expanded, configuration upon deployment from the first shaft. The bag brim includes a spring assembly disposed between the first and second ends thereof that is configured to facilitate automatic expansion of the bag brim to the expanded configuration upon deployment thereof from within the first shaft.

12 Claims, 3 Drawing Sheets

(56) References Cited

U.S. PATENT DOCUMENTS

| | | | |
|---|---|---|---|
| 6,350,266 | B1 | 2/2002 | White et al. |
| 6,350,267 | B1 | 2/2002 | Stefanchik |
| 6,358,198 | B1 | 3/2002 | Levin et al. |
| 6,368,328 | B1 | 4/2002 | Chu et al. |
| 6,383,195 | B1 | 5/2002 | Richard |
| 6,383,197 | B1 | 5/2002 | Conlon et al. |
| 6,387,102 | B2 | 5/2002 | Pagedas |
| 6,406,440 | B1 | 6/2002 | Stefanchik |
| 6,409,733 | B1 | 6/2002 | Conlon et al. |
| 6,447,523 | B1 | 9/2002 | Middleman et al. |
| 6,530,923 | B1 | 3/2003 | Dubrul et al. |
| 6,537,273 | B1 | 3/2003 | Sosiak et al. |
| 6,752,822 | B2 | 6/2004 | Jespersen |
| 6,805,699 | B2 | 10/2004 | Shimm |
| 6,951,533 | B2 | 10/2005 | Foley |
| 6,986,774 | B2 | 1/2006 | Middleman et al. |
| 7,037,275 | B1 | 5/2006 | Marshall et al. |
| 7,052,501 | B2 | 5/2006 | McGuckin, Jr. |
| 7,087,062 | B2 | 8/2006 | Dhindsa |
| 7,101,379 | B2 | 9/2006 | Gregory, Jr. et al. |
| 7,101,380 | B2 | 9/2006 | Khachin et al. |
| 7,112,172 | B2 | 9/2006 | Orban, III et al. |
| 7,115,125 | B2 | 10/2006 | Nakao et al. |
| 7,144,400 | B2 | 12/2006 | Byrum et al. |
| 7,169,154 | B1 | 1/2007 | Que et al. |
| 7,229,418 | B2 | 6/2007 | Burbank et al. |
| 7,285,126 | B2 | 10/2007 | Sepetka et al. |
| 7,316,692 | B2 | 1/2008 | Huffmaster |
| 7,357,801 | B2 | 4/2008 | Burbank et al. |
| 7,534,252 | B2 | 5/2009 | Sepetka et al. |
| 7,547,310 | B2 | 6/2009 | Whitfield |
| 7,615,013 | B2 | 11/2009 | Clifford et al. |
| 7,618,437 | B2 | 11/2009 | Nakao |
| 7,654,283 | B2 | 2/2010 | Seto et al. |
| 7,670,346 | B2 | 3/2010 | Whitfield |
| 7,678,118 | B2 | 3/2010 | Bates et al. |
| 7,722,626 | B2 | 5/2010 | Middleman et al. |
| 7,727,227 | B2 | 6/2010 | Teague et al. |
| 7,731,722 | B2 | 6/2010 | Lavelle et al. |
| 7,731,723 | B2 | 6/2010 | Kear et al. |
| 7,762,959 | B2 | 7/2010 | Bilsbury |
| 7,762,960 | B2 | 7/2010 | Timberlake et al. |
| 7,875,038 | B2 | 1/2011 | Que et al. |
| 7,892,242 | B2 | 2/2011 | Goldstein |
| 7,914,540 | B2 | 3/2011 | Schwartz et al. |
| 7,918,860 | B2 | 4/2011 | Leslie et al. |
| 7,955,292 | B2 | 6/2011 | Leroy et al. |
| 8,057,485 | B2 | 11/2011 | Hollis et al. |
| 8,075,567 | B2 | 12/2011 | Taylor et al. |
| 8,118,816 | B2 | 2/2012 | Teague |
| 8,152,820 | B2 | 4/2012 | Mohamed et al. |
| 8,172,772 | B2 | 5/2012 | Zwolinsk et al. |
| 8,211,115 | B2 | 7/2012 | Cheng et al. |
| 8,282,572 | B2 | 10/2012 | Bilsbury |
| 8,337,510 | B2 | 12/2012 | Rieber et al. |
| 8,348,827 | B2 | 1/2013 | Zwolinski |
| 8,409,216 | B2 | 4/2013 | Parihar et al. |
| 8,414,596 | B2 | 4/2013 | Parihar et al. |
| 8,419,749 | B2 | 4/2013 | Shelton, IV et al. |
| 8,425,533 | B2 | 4/2013 | Parihar et al. |
| 8,430,826 | B2 | 4/2013 | Uznanski et al. |
| 8,435,237 | B2 | 5/2013 | Bahney |
| 8,444,655 | B2 | 5/2013 | Parihar et al. |
| 8,486,087 | B2 | 7/2013 | Fleming |
| 8,512,351 | B2 | 8/2013 | Teague |
| 8,579,914 | B2 | 11/2013 | Menn et al. |
| 8,585,712 | B2 | 11/2013 | O'Prey et al. |
| 8,591,521 | B2 | 11/2013 | Cherry et al. |
| 8,652,147 | B2 | 2/2014 | Hart |
| 8,721,658 | B2 | 5/2014 | Kahle et al. |
| 8,734,464 | B2 | 5/2014 | Grover et al. |
| 8,777,961 | B2 | 7/2014 | Cabrera et al. |
| 8,795,291 | B2 | 8/2014 | Davis et al. |
| 8,821,377 | B2 | 9/2014 | Collins |
| 8,827,968 | B2 | 9/2014 | Taylor et al. |
| 8,870,894 | B2 | 10/2014 | Taylor et al. |
| 8,906,035 | B2 | 12/2014 | Zwolinski et al. |
| 8,956,370 | B2 | 2/2015 | Taylor et al. |
| 8,968,329 | B2 | 3/2015 | Cabrera |
| 8,986,321 | B2 | 3/2015 | Parihar et al. |
| 9,005,215 | B2 | 4/2015 | Grover et al. |
| 9,017,328 | B2 | 4/2015 | Bahney |
| 9,017,340 | B2 | 4/2015 | Davis |
| 9,033,995 | B2 | 5/2015 | Taylor et al. |
| 9,084,588 | B2 | 7/2015 | Farascioni |
| 9,101,342 | B2 | 8/2015 | Saleh |
| 9,113,848 | B2 | 8/2015 | Fleming et al. |
| 9,113,849 | B2 | 8/2015 | Davis |
| 9,308,008 | B2 | 4/2016 | Duncan et al. |
| 9,364,201 | B2 | 6/2016 | Orban, III |
| 9,364,202 | B2 | 6/2016 | Menn et al. |
| 9,370,341 | B2 | 6/2016 | Ceniccola et al. |
| 9,370,378 | B2 | 6/2016 | O'Prey et al. |
| 9,375,224 | B2 | 6/2016 | Jansen |
| 9,414,817 | B2 | 8/2016 | Taylor et al. |
| 9,468,542 | B2 | 10/2016 | Hurley et al. |
| 9,486,188 | B2 | 11/2016 | Secrest et al. |
| 9,522,034 | B2 | 12/2016 | Johnson et al. |
| 9,549,747 | B2 | 1/2017 | Carlson |
| 9,579,115 | B2 | 2/2017 | Kahle et al. |
| 9,592,067 | B2 | 3/2017 | Hartoumbekis |
| 9,622,730 | B2 | 4/2017 | Farascioni |
| 9,624,638 | B2 | 4/2017 | Lebreton et al. |
| 9,629,618 | B2 | 4/2017 | Davis et al. |
| 9,655,644 | B2 | 5/2017 | Collins |
| 9,730,716 | B2 | 8/2017 | Secrest et al. |
| 9,789,268 | B2 | 10/2017 | Hart et al. |
| 9,808,228 | B2 | 11/2017 | Kondrup et al. |
| 9,826,997 | B2 | 11/2017 | Cherry et al. |
| 9,867,600 | B2 | 1/2018 | Parihar et al. |
| 9,877,893 | B2 | 1/2018 | Taylor et al. |
| 2019/0321018 | A1* | 10/2019 | Prior ............... A61B 17/00234 |

* cited by examiner

TISSUE SPECIMEN RETRIEVAL DEVICE WITH REINFORCED SPRING

BACKGROUND

Technical Field

The present disclosure relates to tissue specimen retrieval from an internal body cavity and, more particularly, to tissue specimen retrieval devices and methods to facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is highly desirable to inhibit seeding of cancer cells. Thus, with respect to breaking down large tissue specimens for retrieval through minimally-invasive openings, there is the added challenge of doing so within an enclosed environment. As a result, various specimen retrieval devices have been developed. These devices are typically made from shape memory alloys (e.g., Nitinol®) that are configured to facilitate deployment of the specimen bag and bag brim for specimen retrieval. However, these materials tend to be expensive compared to stainless steel and other materials.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

Provided in accordance with aspects of the present disclosure is a tissue specimen retrieval device including a first shaft and a second shaft telescopically movable relative to the first shaft. The second shaft supports an end effector assembly at a distal end thereof that is movable relative to the first shaft between a retracted position, wherein the end effector assembly is disposed within the first shaft, and a deployed position, wherein the end effector assembly extends distally from the first shaft in an expanded configuration. The end effector assembly includes a bag brim having first and second ends that operably engage the distal end of the second shaft. The bag brim is transitionable from a first collapsed configuration for disposition within the first shaft to an expanded, substantially circular configuration upon deployment from the first shaft. The bag brim includes a spring assembly disposed between the first and second ends thereof that is configured to facilitate automatic expansion of the bag brim to the expanded configuration upon deployment thereof from within the first shaft.

In aspects according to the present disclosure, the spring assembly includes a torsion spring having opposing legs extending therefrom, each leg configured to operably engage one of the first and second ends of the bag brim. In other aspects according to the present disclosure, the spring assembly includes two torsion springs each having opposing legs extending therefrom, each leg of each torsion spring configured to operably engage one of the first and second ends of the bag brim. In yet other aspects according to the present disclosure, the spring assembly includes a rivet and cap arrangement configured to secure the torsion springs between opposing first and second ends of the bag brim.

In aspects according to the present disclosure, each leg of the torsion spring is configured to engage a corresponding slot defined in each of the first and second ends of the bag brim. In other aspects according to the present disclosure, each leg of each respective torsion spring (of a two or more torsion spring arrangement) is configured to engage a corresponding slot defined in each of the first and second ends of the bag brim.

In aspects according to the present disclosure, the bag brim is made from high yield stainless steel, one or more polymers, plastic, composite material, surgical stainless steel, and/or aluminum.

Provided in accordance with aspects of the present disclosure is a tissue specimen retrieval device including a first shaft and a second shaft telescopically movable relative to the first shaft. The second shaft supports an end effector assembly at a distal end thereof and is movable relative to the first shaft between a retracted position, wherein the end effector assembly is disposed within the first shaft, and a deployed position, wherein the end effector assembly extends distally from the first shaft in an expanded configuration. The end effector assembly includes a bag brim having first and second ends that operably engage the distal end of the second shaft. The bag brim is made from a substantially flat material transitionable from a first collapsed configuration for disposition within the first shaft to an expanded, substantially circular configuration upon deployment from the first shaft. The bag brim includes a spring assembly disposed between the first and second ends thereof. The spring assembly includes a torsion spring having opposing legs extending from opposite ends thereof configured to engage corresponding slots defined within the first and second ends of the bag brim. The spring assembly is configured to facilitate automatic expansion of the bag brim to the expanded configuration upon deployment thereof from within the first shaft.

In aspects according to the present disclosure, the spring assembly includes two torsion springs each having opposing legs extending therefrom, each leg of each torsion spring configured to operably engage one of the slots defined in the first and second ends of the bag brim. In other aspects according to the present disclosure, the spring assembly includes a rivet and cap arrangement configured to secure the torsion springs between opposing first and second ends of the bag brim.

In aspects according to the present disclosure, the bag brim is made from high yield stainless steel, one or more polymers, plastic, composite material, surgical stainless steel, and/or aluminum.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
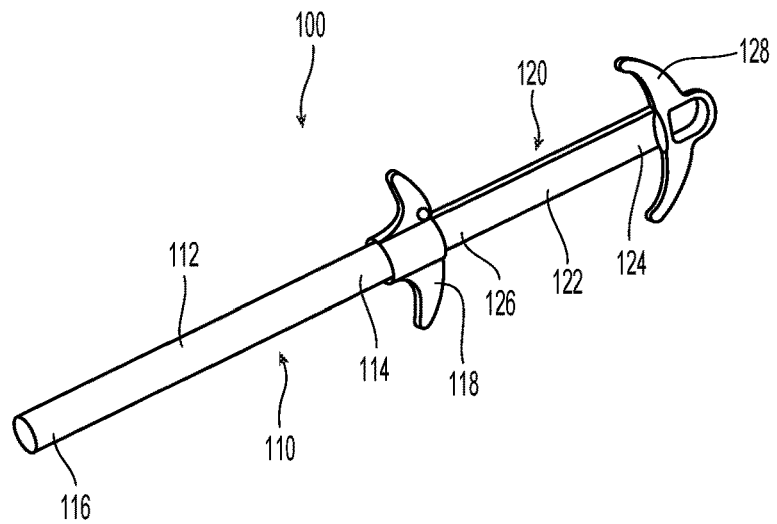
FIG. 1 is a perspective view of a tissue specimen retrieval device provided in accordance with aspects of the present disclosure, disposed in a retracted position.
Figure 2A:
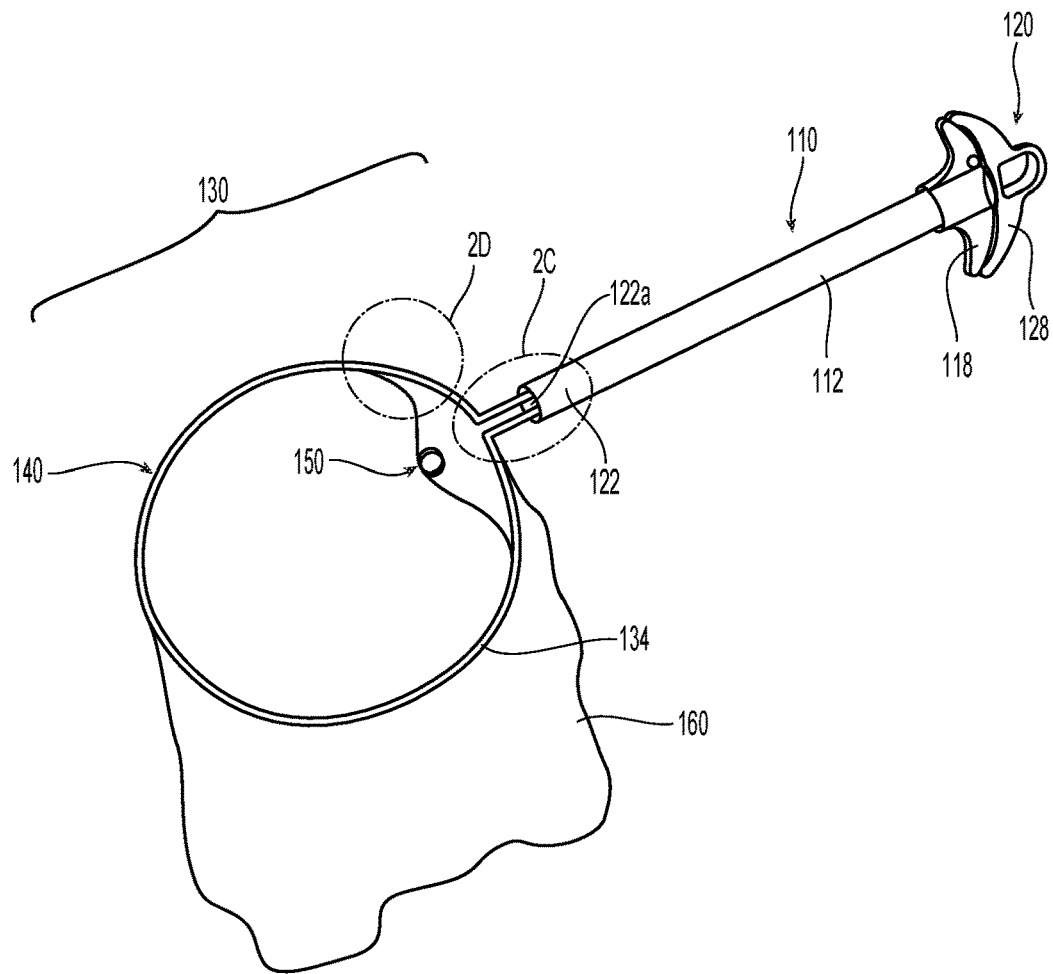
FIG. 2A is a perspective view of the tissue specimen retrieval device of FIG. 1, disposed in a deployed position showing a bag brim supporting a specimen bag.
Figure 2B:
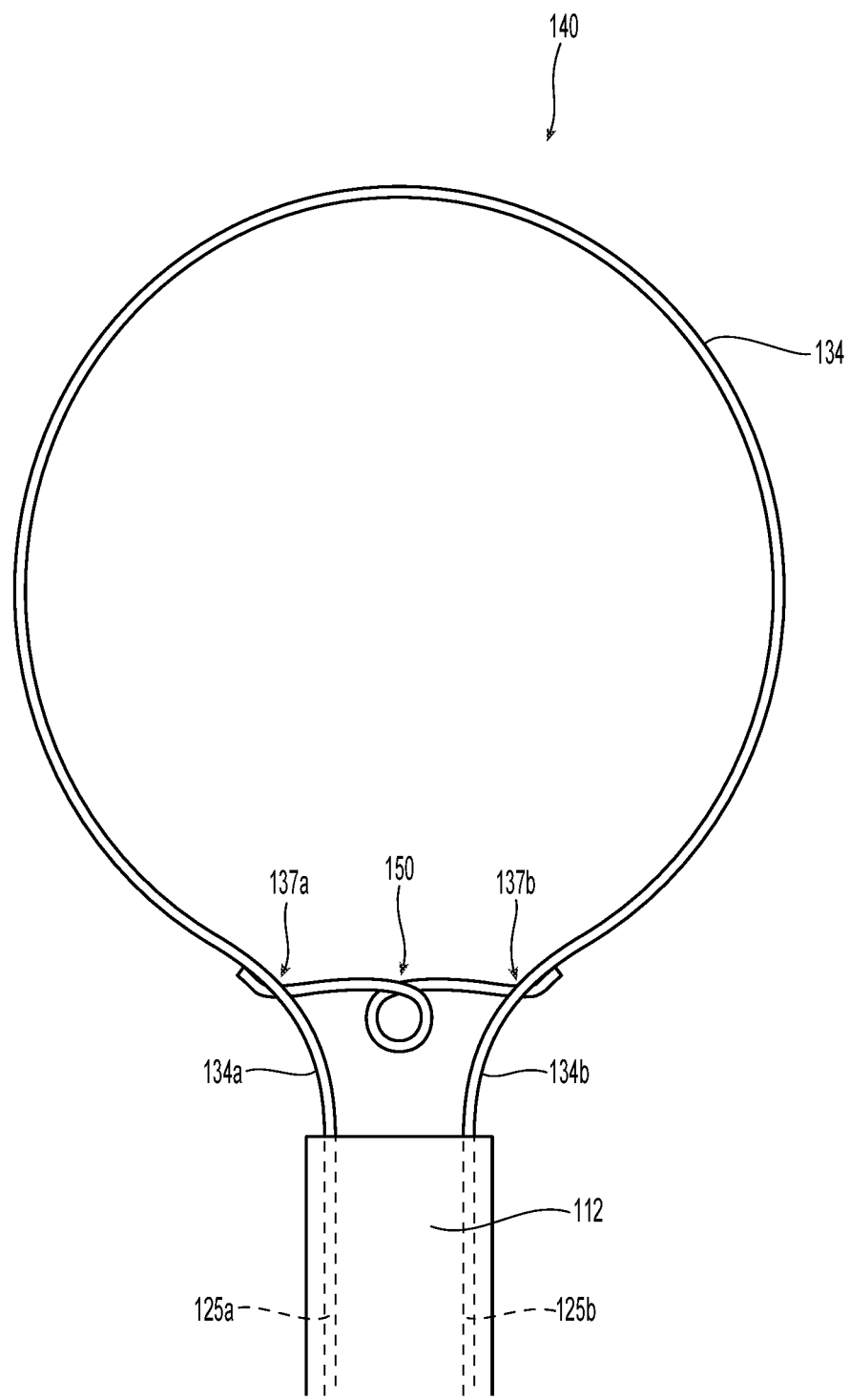
FIG. 2B is a top view of the bag brim of FIG. 2A showing a reinforced spring assembly.
Figure 2C:
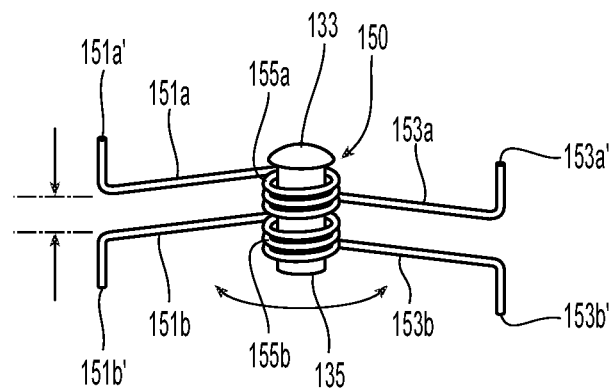
FIG. 2C is an enlarged, stand-alone view of the reinforced spring assembly of FIG. 2B.
Figure 2D:
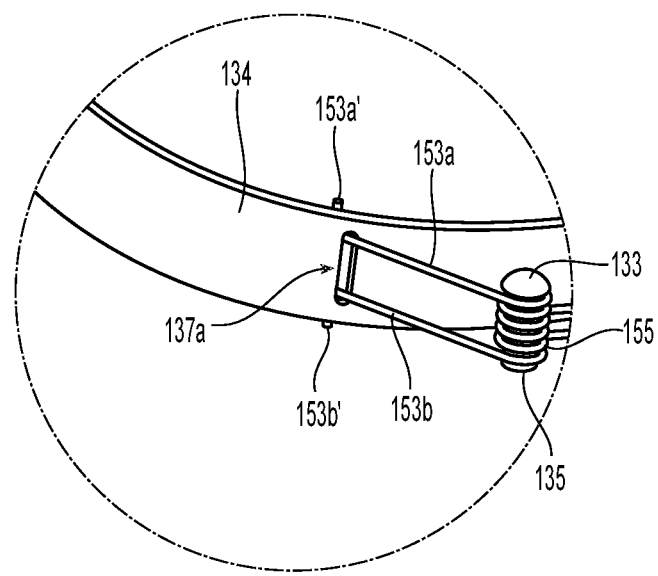
FIG. 2D is an enlarged, side perspective view showing detail of the engagement of the reinforced spring assembly and an arm of the bag brim.

Turning to FIGS. 1-2D, a tissue specimen retrieval device provided in accordance with the present disclosure is shown generally identified by reference numeral 100. Tissue specimen retrieval device 100 includes a first body 110, a second body 120, and an end effector assembly 130 including a bag brim 140 and a specimen bag 160. First body 110 includes a first shaft 112 defining a proximal end portion 114 and a distal end portion 116. First body 110 further includes a first handle 118 disposed at proximal end portion 114 of first shaft 112. First handle 118 may be engaged with proximal end portion 114 of first shaft 112, monolithically formed with proximal end portion 114 of first shaft 112, or otherwise secured thereto in any suitable manner that enables a user to grasp and manipulate first handle 118 to thereby control manipulation of first shaft 112.

Second body 120 includes a second shaft 122 defining a proximal end portion 124 and a distal end portion 126. Second shaft 122 supports end effector assembly 130 at distal end portion 126 of second shaft 122 and is telescopically slidably within and relative to first shaft 112 between a retracted position of tissue specimen retrieval device 100 (FIG. 1), wherein end effector assembly 130 is disposed within first shaft 112, and a deployed position of tissue specimen retrieval device 100 (FIG. 2A), wherein end effector assembly 130 extends distally from first shaft 112 to deploy the bag brim 140 and specimen bag 160. Second body 120 further includes a second handle 128 disposed at proximal end portion 124 of second shaft 122. Second handle 128 may be engaged with proximal end portion 124 of second shaft 122, monolithically formed with proximal end portion 124 of second shaft 122, or otherwise secured thereto in any suitable manner that enables a user to grasp and manipulate second handle 128 to thereby control manipulation of second shaft 122. Second handle 128, more specifically, is movable relative to first handle 118 from a spaced-apart position (FIG. 1) to an approximated position (FIG. 2A) to move tissue specimen retrieval device 100 from the retracted position (FIG. 1), wherein end effector assembly 130 is disposed within first shaft 112, to the deployed position (FIG. 2A), wherein end effector assembly 130 extends distally from first shaft 112.

Referring to FIGS. 2A-2D, end effector assembly 130, as noted above, is supported at distal end portion 126 of second shaft 122. End effector assembly 130, more specifically, includes bag brim 140 extending distally from distal end portion 126 of second shaft 122 and a specimen bag 160 supported on the bag brim 140. Bag brim 140 includes a substantially circular arm 134 that extends from a distal face 122a of shaft 122. Bag brim 140 is typically made from a shape memory alloy (e.g., Nitinol®) that is configured to facilitate deployment of the bag brim 140 for specimen retrieval. Other types of materials may be cheaper to utilize for the bag brim 140, e.g., polymers, plastics, composite materials, surgical stainless steel, aluminum, etc., but may need to be reinforced with a spring assembly, e.g., spring assembly 150 described below, to insure reliable deployment. Moreover, the bag brim 140 may be designed to be substantially flat (e.g., thin, band-like material) to provide strength for supporting the specimen bag 160 while still being flexible to facilitate expansion and retraction thereof.

For example and as best shown in FIGS. 2A-2D, bag brim 140 is made from high yield stainless steel that may be heat treated after initial shaping. More specifically, arm 134 includes free ends 134a and 134b that each operably engage a corresponding aperture 125a, 125b defined within the distal face 122a of the second shaft 122 (either selectively engaged or are affixed therein) to form a band-like support for supporting the specimen bag 160.

With continued reference to FIGS. 2A-2D, arm 134 of bag brim 140 includes a spring assembly 150 disposed between free ends 134a, 134b proximate the distal end 122 of shaft 112. Spring assembly 150 includes one or more torsion springs 155a, 155b disposed about a rivet 133 and cap 135 arrangement. Each torsion spring 155a, 155b includes a pair of corresponding legs 151a, 153a, and 151b, 153b, respectively, that extend from opposite sides thereof. Each leg 151a, 153a and 151b, 153b of each respective torsion spring 155a, 155b includes a corresponding hook 151a', 153a' and 151b', 153b' at a distal end thereof. Distal ends 151a', 151b' are configured to engage a slot 137a defined in free end 134a (FIGS. 2B and 2D) and distal ends 153a', 153b' are configured to engage a slot 137b defined in free end 134b (FIG. 2B). A single torsion spring, e.g., 155a, may also be utilized depending upon a particular purpose.

When used in this fashion, the torsion springs 155a, 155b cooperate with respective legs 151a, 153a and 151b, 153b to allow the specimen bag 160 to unfurl (FIGS. 2A and 2B) quickly and easily when the bag brim 140 is deployed from the first shaft 112. Likewise the torsion springs 155a, 155b allow the specimen bag 160 to be collapsed (FIG. 1) in a similar, albeit, reversed, fashion.

More particularly and as shown by the arrows in FIG. 2B, the positioning of the torsion spring 155a, 155b on the bag brim 140 facilitates automatic expansion of bag brim 140 and unfurling of the specimen bag 160 when the bag brim 140 is deployed from the first shaft 112 upon approximation of the first handle 118 proximally relative to the second handle 128. Moreover, the surgeon can collapse the bag brim 140 and specimen bag 160 by simply squeezing the bag brim 140 against the bias of torsion springs 155a, 155b to collapse the bag brim 140 for reinsertion within first shaft 112.

Turning now to FIG. 2C, a rivet 133 may be utilized to secure the two torsions springs 155a, 155b together on the bag brim 140 to maintain alignment and to provide a common pivot axis therethrough. During assembly, the rivet 133 is inserted through each torsion spring 155a, 155b and a rivet cap 135 is utilized to secure the rivet 133 thereto. Heat shrink tubing (not shown) may be utilized over the torsion springs 155a, 155b to reduce the chances of the torsion springs 155a, 155b pinching tissue or to reduce possible specimen bag 160 tears.

A plurality of spring assemblies 150 (not shown) may be utilized around the bag brim 140 depending upon a particular purpose.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval device, comprising:
a first shaft;
a second shaft telescopically movable relative to the first shaft, the second shaft supporting an end effector assembly at a distal end thereof and movable relative to the first shaft between a retracted position, wherein the end effector assembly is disposed within the first shaft, and a deployed position, wherein the end effector assembly extends distally from the first shaft in an expanded configuration, the end effector assembly including:
a bag brim having first and second ends that operably engage the distal end of the second shaft, the bag brim transitionable from a first collapsed configuration for disposition within the first shaft to an expanded, substantially circular configuration upon deployment from the first shaft, the bag brim including a spring assembly disposed between the first and second ends thereof, the spring assembly configured to facilitate automatic expansion of the bag brim to the expanded configuration upon deployment thereof from within the first shaft, wherein the spring assembly includes a torsion spring having opposing legs extending therefrom, each leg configured to operably engage one of the first or second ends of the bag brim and wherein each leg of the torsion spring is configured to engage a corresponding slot defined in each of the first and second ends of the bag brim.

2. The tissue specimen retrieval device according to claim 1 wherein the spring assembly includes two torsion springs each having opposing legs extending therefrom, each leg of each torsion spring configured to operably engage one of the first and second ends of the bag brim.

3. The tissue specimen retrieval device according to claim 2 wherein the spring assembly includes a rivet and cap arrangement configured to secure the torsion springs between opposing first and second ends of the bag brim.

4. The tissue specimen retrieval device according to claim 2 wherein each leg of each respective torsion spring is configured to engage a corresponding slot defined in each of the first and second ends of the bag brim.

5. The tissue specimen retrieval device according to claim 1 wherein the bag brim is made from at least one of high yield stainless steel, one or more polymers, plastic, composite material, surgical stainless steel, or aluminum.

6. A tissue specimen retrieval device, comprising:
a first shaft;
a second shaft telescopically movable relative to the first shaft, the second shaft supporting an end effector assembly at a distal end thereof and movable relative to the first shaft between a retracted position, wherein the end effector assembly is disposed within the first shaft, and a deployed position, wherein the end effector assembly extends distally from the first shaft in an expanded configuration, the end effector assembly including:
a bag brim having first and second ends that operably engage the distal end of the second shaft, the bag brim made from a substantially flat material transitionable from a first collapsed configuration for disposition within the first shaft to an expanded, substantially circular configuration upon deployment from the first shaft, the bag brim including a spring assembly disposed between the first and second ends thereof, the spring assembly including a torsion spring including opposing legs extending from opposite ends thereof configured to engage corresponding slots defined within the first and second ends of the bag brim, the spring assembly configured to facilitate automatic expansion of the bag brim to the expanded configuration upon deployment thereof from within the first shaft.

7. The tissue specimen retrieval device according to claim 6 wherein the spring assembly includes two torsion springs each having opposing legs extending therefrom, each leg of each torsion spring configured to operably engage one of the slots defined in the first and second ends of the bag brim.

8. The tissue specimen retrieval device according to claim 7 wherein the spring assembly includes a rivet and cap arrangement configured to secure the torsion springs between opposing first and second ends of the bag brim.

9. The tissue specimen retrieval device according to claim 6 wherein the bag brim is made from at least one of high yield stainless steel, one or more polymers, plastic, composite material, surgical stainless steel, or aluminum.

10. A tissue specimen retrieval device, comprising:
a first shaft;
a second shaft telescopically movable relative to the first shaft, the second shaft supporting an end effector assembly at a distal end of the second shaft and movable relative to the first shaft between a retracted position, wherein the end effector assembly is disposed within the first shaft, and a deployed position, wherein the end effector assembly extends distally from the first shaft in an expanded configuration, the end effector assembly including:
a bag brim having first and second ends that operably engage the distal end of the second shaft, the bag brim transitionable from a collapsed configuration for disposition within the first shaft to an expanded, substantially circular configuration upon deployment from the first shaft, the bag brim including a spring assembly disposed between the first and second ends of the bag brim, the spring assembly configured to facilitate automatic expansion of the bag brim to the expanded configuration upon deployment of the spring assembly from within the first shaft, wherein the spring assembly includes two torsion springs each having opposing legs extending from the spring assembly, each leg of each torsion spring configured to operably engage one of the first or second ends of the bag brim and wherein each leg of each respective torsion spring is configured to engage a corresponding slot defined in each of the first and second ends of the bag brim.

11. The tissue specimen retrieval device according to claim 10, wherein the bag brim is made from at least one of high yield stainless steel, one or more polymers, plastic, composite material, surgical stainless steel, or aluminum.

12. The tissue specimen retrieval device according to claim 10, wherein the spring assembly includes a rivet and cap arrangement configured to secure the torsion springs between opposing first and second ends of the bag brim.

* * * * *